(12) United States Patent
Eskuri et al.

(10) Patent No.: US 8,162,974 B2
(45) Date of Patent: Apr. 24, 2012

(54) OCCLUSION APPARATUS, SYSTEM, AND METHOD

(75) Inventors: Alan Eskuri, Hanover, MN (US); Anthony C. Vrba, Maple Grove, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 516 days.

(21) Appl. No.: 11/345,832

(22) Filed: Feb. 2, 2006

(65) Prior Publication Data

US 2007/0179527 A1 Aug. 2, 2007

(51) Int. Cl.
*A61B 17/08* (2006.01)
*A61D 1/00* (2006.01)

(52) U.S. Cl. ........................................ 606/213; 606/215

(58) Field of Classification Search .................. 606/213, 606/215–218, 139, 151; 411/508–510; 24/90.1, 24/91, 94, 108; 403/104, 105
See application file for complete search history.

(56) References Cited

U.S. PATENT DOCUMENTS

| | | | | |
|---|---|---|---|---|
| 283,653 | A | * | 8/1883 | Paxson ............................ 411/338 |
| 3,874,388 | A | * | 4/1975 | King et al. ....................... 606/232 |
| 4,007,743 | A | | 2/1977 | Blake |
| 5,284,488 | A | | 2/1994 | Sideris |
| 5,334,217 | A | | 8/1994 | Das |
| 5,342,393 | A | * | 8/1994 | Stack ............................... 606/213 |
| 5,350,399 | A | * | 9/1994 | Erlebacher et al. ............ 606/213 |
| 5,433,727 | A | | 7/1995 | Sideris |
| 5,578,045 | A | | 11/1996 | Das |
| 5,591,206 | A | * | 1/1997 | Moufarrege .................... 606/215 |
| 5,634,936 | A | | 6/1997 | Linden et al. |
| 5,702,421 | A | | 12/1997 | Schneidt |
| 5,709,707 | A | | 1/1998 | Lock et al. |
| 5,741,297 | A | | 4/1998 | Simon |
| 5,853,422 | A | * | 12/1998 | Huebsch et al. ................ 606/215 |
| 5,879,366 | A | | 3/1999 | Shaw et al. |
| 5,976,174 | A | | 11/1999 | Ruiz |
| 6,024,756 | A | | 2/2000 | Huebsch et al. |
| 6,077,281 | A | | 6/2000 | Das |
| 6,077,291 | A | | 6/2000 | Das |
| 6,080,182 | A | | 6/2000 | Shaw et al. |
| 6,117,159 | A | | 9/2000 | Huebsch et al. |
| 6,206,907 | B1 | | 3/2001 | Marino et al. |
| 6,270,515 | B1 | | 8/2001 | Linden et al. |
| 6,312,446 | B1 | | 11/2001 | Huebsch et al. |

(Continued)

FOREIGN PATENT DOCUMENTS

EP 0 623 003 3/1999

(Continued)

OTHER PUBLICATIONS

International Search Report (6 pgs.).

*Primary Examiner* — Corrine M McDermott
*Assistant Examiner* — Dianne Dornbusch
(74) *Attorney, Agent, or Firm* — Brooks, Cameron & Huebsch, PLLC

(57) ABSTRACT

Methods, apparatus, and systems for occluding a defective occlusion. Methods, apparatus, and systems include the use of an occlusion device having occluder pads. The distance between the occluder pads can be adjusted so as to compress tissue between the occluder pads to anchor the occlusion device to the tissue and to block the defective occlusion.

21 Claims, 7 Drawing Sheets

U.S. PATENT DOCUMENTS

| | | | |
|---|---|---|---|
| 6,379,368 B1 | 4/2002 | Corcoran et al. | |
| 6,548,569 B1 | 4/2003 | Williams et al. | |
| 6,838,493 B2 | 1/2005 | Williams et al. | |
| 6,867,247 B2 | 3/2005 | Williams et al. | |
| 2002/0156150 A1 | 10/2002 | Williams et al. | |
| 2002/0173558 A1 | 11/2002 | Williams et al. | |
| 2002/0183787 A1 | 12/2002 | Wahr et al. | |
| 2003/0055455 A1* | 3/2003 | Yang et al. | 606/215 |
| 2004/0002764 A1* | 1/2004 | Gainor et al. | 623/17.16 |
| 2004/0073242 A1 | 4/2004 | Chanduszko | |
| 2004/0133206 A1* | 7/2004 | Stevens et al. | 606/72 |
| 2004/0133236 A1 | 7/2004 | Chanduszko | |
| 2004/0254625 A1 | 12/2004 | Stephens et al. | |
| 2005/0021016 A1 | 1/2005 | Malecki et al. | |
| 2005/0043759 A1 | 2/2005 | Chanduszko | |
| 2005/0065548 A1* | 3/2005 | Marino et al. | 606/213 |
| 2005/0107578 A1 | 5/2005 | Williams et al. | |
| 2005/0131401 A1 | 6/2005 | Malecki | |
| 2005/0137452 A1 | 6/2005 | Osypka | |
| 2005/0192627 A1 | 9/2005 | Whisenant et al. | |
| 2005/0273135 A1* | 12/2005 | Chanduszko et al. | 606/213 |
| 2006/0122647 A1* | 6/2006 | Callaghan et al. | 606/213 |

FOREIGN PATENT DOCUMENTS

| | | |
|---|---|---|
| EP | 0 861 049 | 4/2001 |
| EP | 0 961 579 | 8/2005 |
| WO | WO 93/13712 | 7/1993 |
| WO | WO 95/28885 | 11/1995 |
| WO | WO 97/16119 | 5/1997 |
| WO | WO 97/42878 | 11/1997 |
| WO | WO 98/08462 | 3/1998 |
| WO | WO 98/27868 | 7/1998 |
| WO | WO 99/40849 A1 | 8/1999 |
| WO | WO 00/56376 | 9/2000 |
| WO | WO 03/103476 | 12/2003 |
| WO | WO 2004/112656 | 12/2004 |
| WO | WO 2005/006990 | 1/2005 |
| WO | WO 2005/027752 | 3/2005 |

* cited by examiner

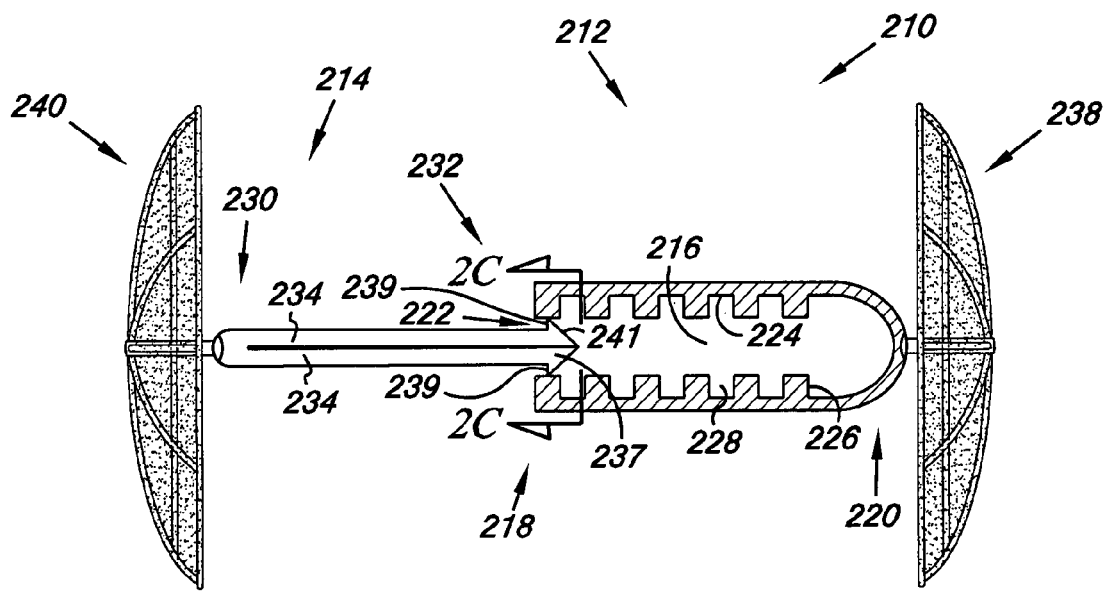
*Fig. 2A*
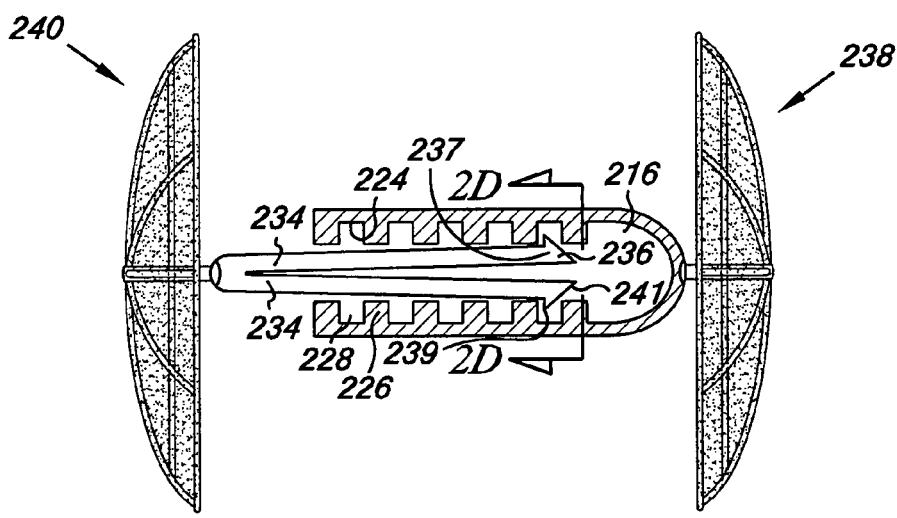
*Fig. 2B*
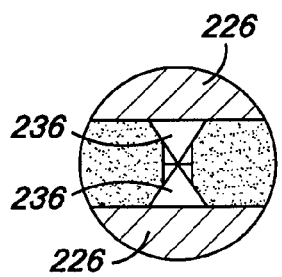 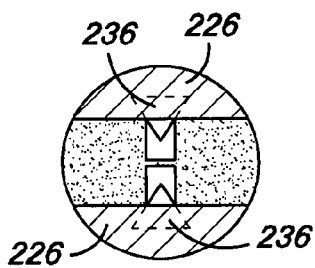
*Fig. 2C*     *Fig. 2D*

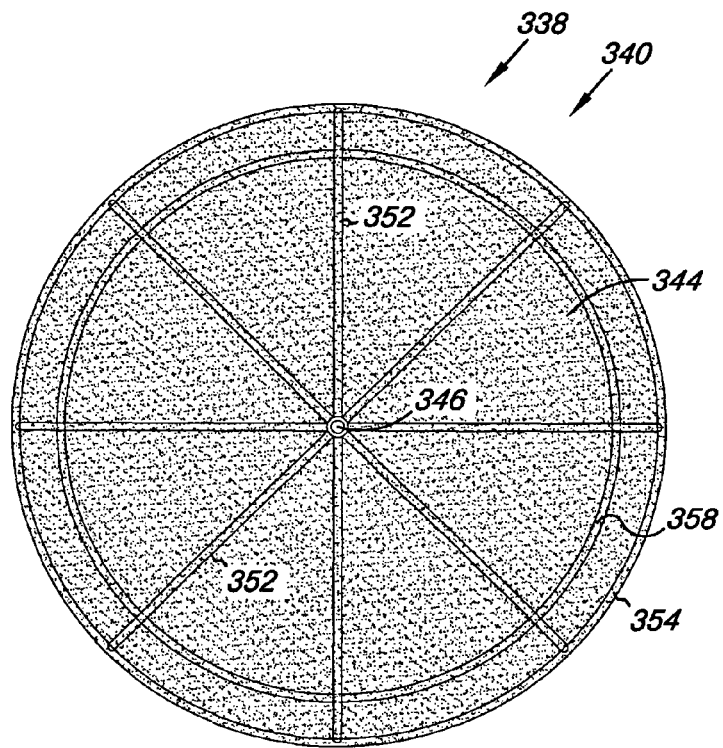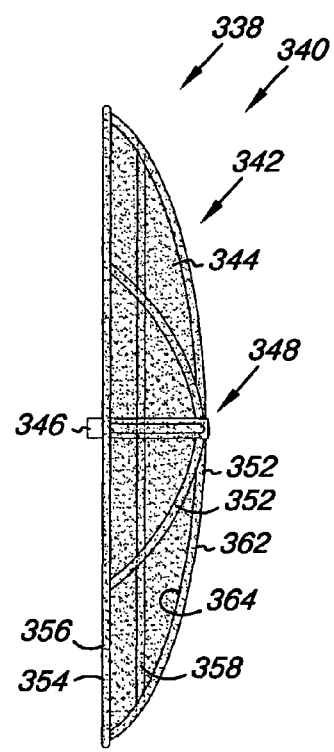
*Fig. 3A*  *Fig. 3B*
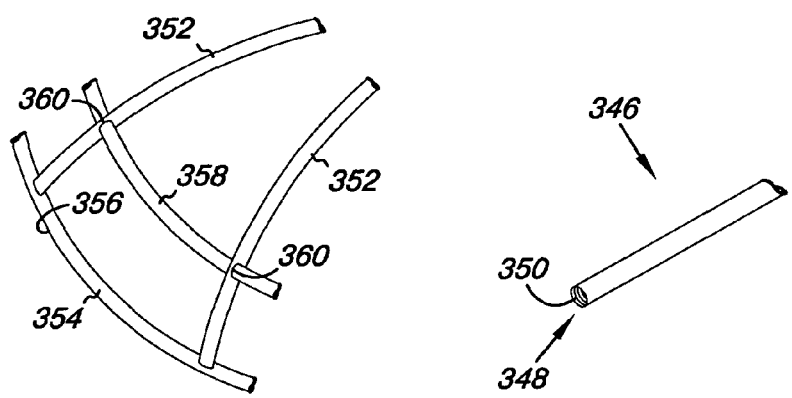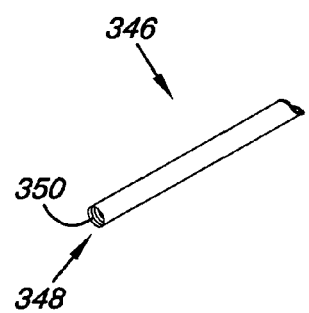
*Fig. 3C*  *Fig. 3D*

OCCLUSION APPARATUS, SYSTEM, AND METHOD

FIELD OF THE INVENTION

The present invention relates generally to apparatus, systems, and methods for use in the human body, more particularly to apparatus, systems, and methods to close a defective occlusion in the heart.

BACKGROUND

The human heart is divided into four chambers. These include the right atrium, the right ventricle, the left atrium, and the left ventricle. The right atrium and right ventricle are divided from the left atrium and left ventricle by a muscular wall call the septum. The atrial septum is the wall separating the atria and the ventricular septum is the wall separating the ventricles.

Several occlusion defects exists which can affect the septa of both children and adults. Example of such occlusion defects can include patent ductus arteriosus, patent foramen ovale (PFOs), atrial septal defects (ASDs), and ventricular septal defects (VSDs). Although the causes and physical characteristics of these defects can vary, each of these defects is generally a small passage, flap, or hole in the septum which allows blood to shunt between chambers in the heart where there is generally no blood flow in a normal, healthy heart. Shunting of this type can result in a number of health problems.

BRIEF DESCRIPTION OF THE DRAWINGS

FIGS. 2A-2D illustrate an embodiment of an occlusion device according to the present invention.

FIG. 3A-3D illustrate an embodiment of an occluder pad according to the present invention.

DETAILED DESCRIPTION

Figure 1:
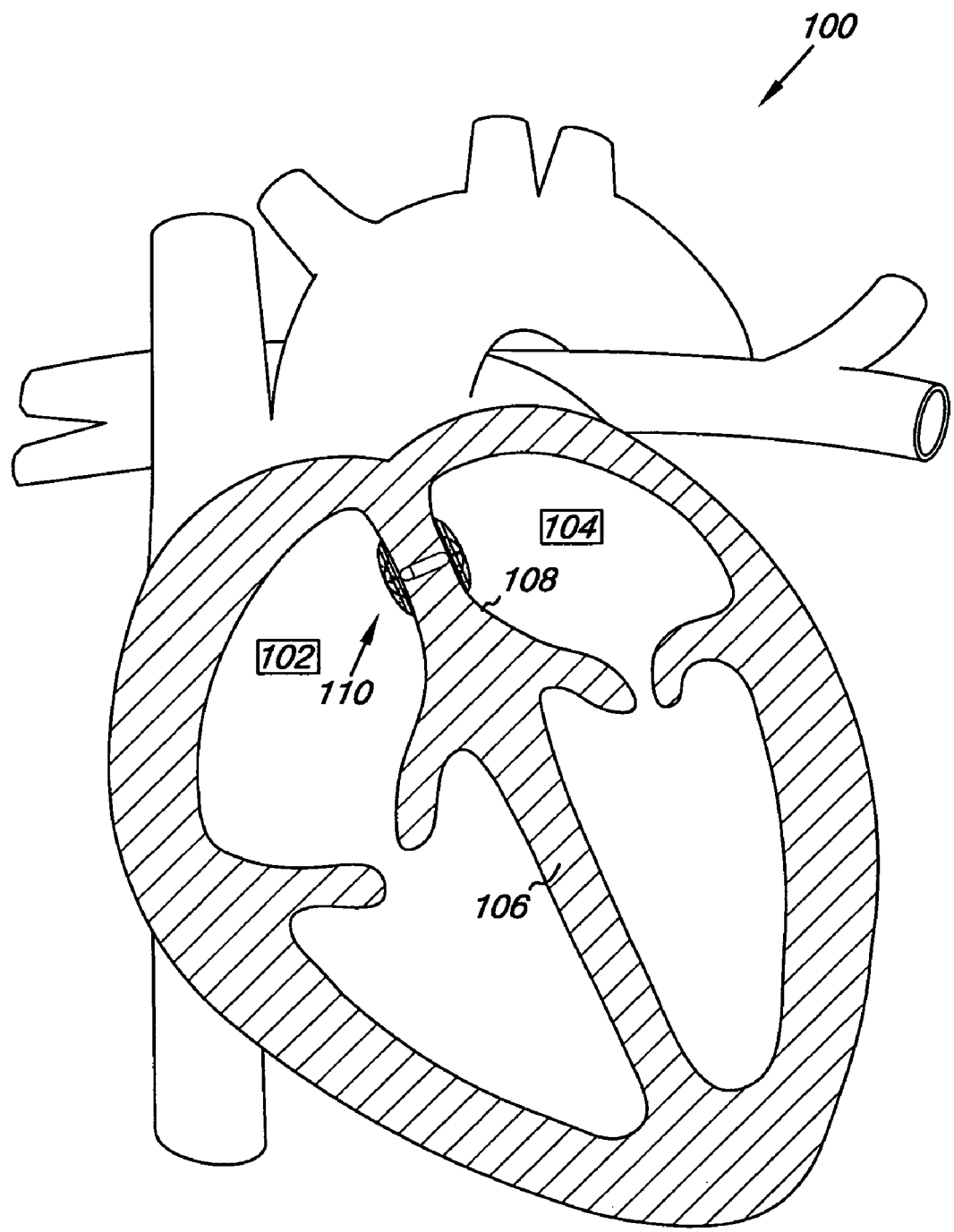
FIG. 1 illustrates a cross-sectional view of the heart having an occlusion device attached to the atrial septum.

Embodiments of the present invention are directed to methods, apparatus, and systems for blocking defective occlusions, such as vascular or septal defects. For example, occluding a defective occlusion can be accomplished through the use of an occlusion device delivered to the defective occlusion by a delivery catheter. The occlusion device can be positioned in such a way that first and second occluder pads coupled to first and second elongate bodies of the occlusion device can be deployed and positioned on each side of the defective occlusion. Once deployed, the first and second elongate bodies can be manipulated so as to adjust a distance between the first and second occluder pads and to secure the adjusted distance. In various embodiments, adjusting the distance can include decreasing the distance between the first and second occluder pads until the occluder pads engage tissue surfaces surrounding each side of the defective occlusion. The occluder pads can then be adjusted to anchor the first and second occluder pads to the tissue and to block the defective occlusion with the first and second occluder pads.

The figures herein follow a numbering convention in which the first digit or digits correspond to the drawing figure number and the remaining digits identify an element or component in the drawing. Similar elements or components between different figures may be identified by the use of similar digits. For example, 110 may reference element "10" in FIG. 1, and a similar element "10" may be referenced as 210 in FIG. 2. As will be appreciated, elements shown in the various embodiments herein can be added, exchanged, and/or eliminated so as to provide a number of additional embodiments of the occlusion device according to the present invention.

The method, apparatus, and system embodiments described herein are illustrated with reference to occluding a patent foramen ovale (PFO), which is an opening in the atrial septum at the location of the fossa ovalis. The method, apparatus, and system embodiments can also be used to occlude other defective occlusions. For example, using the various method, apparatus, and system embodiments described herein, other defective occlusions such as patent ductus arteriosus, atrial septal defects (ASDs), and ventricular septal defects (VSDs) can be occluded.

FIG. 1 illustrates a cross-sectional view of a heart 100. The heart 100 is divided into four chambers, which are referred to herein as the right atrium 102, a right ventricle, a left atrium 104 and a left ventricle. Heart 100 also includes a ventricular septum 106 that divides the left and right ventricle chambers of the heart. The portion of the septal wall dividing the left and right atriums 102 and 104 is the atrial septum 108.

Also shown in FIG. 1 is an occlusion device 110 according to an embodiment of the present invention. In the various embodiments described herein, the occlusion device 110 can be used to occlude a defective occlusion, such as a PFO, by attaching the occlusion device 110 to tissue surrounding opposing sides of the defective occlusion. As will be described herein, once the occlusion device 110 is positioned, it can be anchored to the atrial septum 108 through compression forces applied to the tissue surrounding opposing sides of the PFO and can block the flow of blood and other substances through the PFO to other areas of the heart.

FIGS. 2A-5 illustrate a number of occlusion device embodiments. In FIGS. 2A-5, the occlusion device embodiments have various differences. For example, some embodiments include different structures for adjusting a distance between components coupled to the occlusion device.

In FIGS. 2A-2F, there is illustrated one embodiment of the occlusion device 210 of the present invention. The occlusion device 210 includes a first elongate body 212 and a second elongate body 214. The first elongate body 212 includes a lumen 216 extending between a proximal end 218 and a distal end 220 of the first elongate body 212. The first elongate body 212 includes an opening 222. The opening 222 is in communication with lumen 216. In various embodiments, components of the occlusion device 210 can extend through the opening 222 and within the lumen 216. For example, in various embodiments, the second elongate body 214 can enter through opening 222 and move within lumen 216 of the first elongate body 212. As will be discussed herein, this movement allows a distance between first and second occluder pads 238 and 240 coupled to the first and second elongate bodies to be adjusted.

In various embodiments, surfaces of the lumen 216 define first engaging elements 224. As shown in FIG. 2A, the first engaging elements 224 can be positioned along and extend along the lumen 216 from the opening 222 toward the distal end 220 of the first elongate body 212. In various embodiments, the first engaging elements 224 include surfaces defining a number of projections 226 and indentations 228. As shown in FIG. 2A, the projections 226 and indentations 228 are symmetrically arranged along a longitudinal axis of the first elongate body 212, such that each indentation 228 and each projection 226 alternate along the longitudinal axis. As will be discussed herein, the first engaging elements 224 of the first elongate body 212 and a second engaging element 236 of the second elongate body 214 can interact to adjust the distance between the first and second occluder pads 238 and 240 and to secure the adjusted distance.

The second elongate body 214 has a proximal end 230 and a distal end 232. In the embodiment shown in FIG. 2A, the second elongate body 214 includes two elongate members 234 having a predefined shape. In one embodiment, the elongate members 234 diverge away from each other as they extend from the proximal end 230 toward the distal end 232 of the second elongate body 214. As shown in FIG. 2B, as the elongate members 234 extend toward the distal end 232 of the second elongate body 214, the distance between the elongate members increases such that at the distal end 232 of the second elongate body 214, the distance between the elongate members 234 is larger relative to their distances at the proximal end 230 of the second elongate body 214. As will be discussed herein, the predefined shape of the second elongate body allows the elongate members to expand away from each other when they are not being constrained by the first engaging elements 224 of the first elongate body 212.

The second elongate body 214 includes the second engaging element 236. As used herein, the second engaging element can include various surfaces that define surface structures, designs, and configurations that can interact with the first engaging elements 224 of the first elongate body 212. In some embodiments, the first and second engaging elements 224 and 236 can interact to adjust a distance between the first occluder pad 238 and the second occluder pad 240. For example, the second engaging element 236 of the second elongate member 214 can be moved within the lumen 216 of the first elongate body 212. The second engaging element 236 and the first engaging elements 224 can then interact to allow a distance between the first and second occluder pads 238 and 240 coupled to the first and second elongate bodies 212 and 214, respectively, to be adjusted.

In the embodiments illustrated in FIGS. 2A-2D, the interaction between the first and second engaging elements 224 and 236 of the first and second elongate bodies 212 and 214 can also function to secure the adjusted distance between the first and second occluder pads 238 and 240. In one embodiment, the interaction between surfaces of the first engaging and second engaging elements 224 and 236 can prevent the second elongate body 214 from moving away from the distal end 220 of the first elongate body 212. For example, as shown in FIG. 2B, the second engaging element 236 includes a flange 237 having a locking surface 239 and a compression surface 241.

As illustrated in FIG. 2B, the locking surface 239 of the second engaging element 236 can engage the surface defining the projection 226 of the first engaging members 224 to lock the second elongate body 214 within the lumen 216 of the first elongate body 212. This locking can preclude the second elongate body 214 from moving away from the distal end 220 of the first elongate body 212 so as to secure the distance between the first and second occluder pads 238 and 240 coupled to the first and second elongate bodies 212 and 214. In one embodiment, this can occur as each elongate member 234 of the second elongate body 214 expands away from each other in their unconstrained state to position the second engaging element 236 in the indentation 228 of the first elongate body 212.

As the second elongate body 214 is moved through the lumen 216 of the first elongate body 212 toward the distal end 220 of the first elongate body 212, the compression surface 241 of the second engaging element 236 contacts the surface defining the projection 226. As illustrated, the compression surface 241 is sloped so that the compression surface 241 contacts the projection 226 at an oblique angle (e.g., an acute angle) and can slide past the projection 226 as the two elongate members 234 compress. Once the compression surface 241 passes the projection 226 the two elongate members 234 re-expand to engage the locking surface 239 with the projections 226.

As illustrated, the compression surface 241 can have a planar configuration that contacts a correspondingly planar surface of the projection 226. Alternatively, other shapes for the compression surface 241 and the projection 226 are possible, where the shape of the compression surface 241 and the projection 226 interact to prevent relative radial motion of the first and second elongate members 212 and 214.

In various embodiments, the first and second elongate bodies 212 and 214 can each include a variety of cross-sectional shapes. For example, in the embodiments shown in FIGS. 2A-2D, the elongate members 234 of the second elongate body 214 include a planar cross-sectional shape. In various embodiments however, the elongate members 234 can include other cross-sectional shapes, for example, circular, ovular, and polygonal cross-sectional shapes, among others.

The various components of the occlusion device 212 can be formed of a variety of materials. For example, in one embodiment, the first and second elongate bodies 212 and 214 can be formed from a biocompatible metal, metal alloy, polymeric material, or combination thereof. Examples of suitable materials for the first and second elongate bodies include, but are not limited to, plastics, medical grade stainless steel (e.g., 316L), titanium, tantalum, platinum alloys, niobium alloys, cobalt alloys, alginate, or combinations thereof. In one embodiment, the elongate members 234 of the second elongate body 214 can be formed of shape memory metals such as Nitinol, and/or shape memory polymers. These materials can allow for forming and setting the predefined shape of the elongate members 234, as discussed herein.

FIGS. 3A-3D illustrate an embodiment of the occluder pads 338, 340 of the present invention. Specifically, FIG. 3A illustrates a top-down view of the first and second occluder pad 338, 340. FIG. 3B illustrates a side-on view of the first and second occluder pads 338, 340. FIG. 3C illustrates a support band 358 used with the occluder pads 338, 340 of the present invention. And, FIG. 3D illustrates a center shaft 346 of the present invention.

In various embodiments, the first and second elongate bodies each include an occluder pad coupled thereto. In the various embodiments described herein, the occluder pads function to anchor the occlusion device to a defective occlusion and to block an opening in a defective occlusion, as will be discussed herein.

In the various embodiments of the present invention, the first and second occluder pads are substantially identical. Thus, the following description of the various features of the first and second occluder pads applies to both pads. Where features of the occluder pads differ, the difference will be described.

The various embodiments of the occluder pads can include a variety of designs and configurations, and as such, the following description is not meant to limit the occluder pads to the embodiment illustrated in FIGS. 3A-3C, but rather, to illustrate one of the many embodiments of the occluder pads.

Referring now to FIGS. 3A and 3B, the first and second occluder pads 338 and 340 include a collapsible frame 342 and a cover 344. The collapsible frame 342 is designed to collapse under compression so that it can be inserted into a lumen of a catheter, sheath, and the like, as will be discussed herein. In one embodiment, the collapsible frame 342 defines a circular configuration of the first and second occluder pads 338 and 340. In various embodiments, the collapsible frame 342 can define other configurations, such as an ovular or polygonal collapsible frame.

The collapsible frame 342 includes a center shaft 346. The center shaft 346 includes an elongate structure that defines an apex 348 of the first and second occluder pads 338 and 340. The center shaft 346 of the first occluder pad 338 extends from the apex 348 toward the distal end of the first elongate body, as discussed herein. The center shaft 346 of the second occluder pad 340 extends from the apex 348 toward the proximal end of the second elongate body, as discussed herein.

In various embodiments, the center shaft 346 can include various structures and designs that function to couple a deployment shaft to the center shaft 346. As will be discussed herein, the deployment shaft can be coupled to the center shaft of the second occluder pad to allow an operator to manipulate the occlusion device to adjust the distance between the first and second occluder pads, as well as to lock the second elongate body within the lumen of the first elongate body.

For example, in one embodiment, the center shaft 346 of the second occluder pad 340 can include a lumen that extends from the apex 348 toward the proximal end of the second elongate body. The lumen of the center shaft 346 can include a surface that defines threads 350, as shown in FIG. 3D. As will be discussed herein, the deployment shaft can include an outer surface that defines corresponding threads that can thread with the threads of the center shaft 346 of the second occluder pad 340 to move the second elongate body into the lumen of the first elongate body and to deploy the occlusion device from a catheter.

In various embodiments, the collapsible frame 342 can include a number of struts 352. In the embodiment shown in FIG. 3A, the collapsible frame 342 includes eight struts 352. In various embodiments, the struts 352 can extend radially from the apex 348 of the center shaft 346 and downward toward a circumferential ring member 354. In various embodiments, each strut 352 defines a convex curve as it extends downward from the apex 348 toward the circumferential ring member 354, where it couples to the circumferential ring member 354. In one embodiment, the struts 352 are in a substantially fixed distance relationship around the circumferential ring member 354. As used herein, a substantially fixed distance relationship indicates a fixed distance between the eight struts 352 that may include variations of the fixed distance relationship and thus, need not be consistent around the circumferential ring 354.

In various embodiments, the struts 352 can be coupled to the center shaft 346 and the circumferential ring member 354 in a variety of ways. In one embodiment, the apex 348 of center shaft 346 can include slots for coupling the struts to the center shaft 346. In another embodiment, the apex 348 can include openings through which the struts 352 can pass to thereby couple the struts 352 to the center shaft 346. In various embodiments, the struts 352 can be chemically welded or heat welded to the apex 348 of the center shaft 346 and the circumferential ring member 354. Other methods and/or structures for coupling the struts 352 to the center shaft 346 and the circumferential ring member 354 are also possible.

In one embodiment, the circumferential ring member 354 is a unitary structure having a ring configuration that extends around the first and second occluder pad 338 and 340. As will be discussed herein, the circumferential ring defines a tissue/occluder interface in which the first and second occluder pads compress tissue surrounding a defective occlusion. In one embodiment, the circumferential ring member 354 can be formed of a resilient material that can flex under compression forces so as to deform when the first and second occluder pad 338 and 340 are positioned within a lumen of a catheter, as will be discussed herein. As shown in FIG. 3C, the circumferential ring member 354 includes a circular cross-sectional shape. In various embodiments, the cross-sectional shape of the circumferential ring member can vary. Examples can include, but are not limited to, semi circular, ovular, polygonal, and planar cross-sectional shapes.

In various embodiments, the circumferential ring member 354 can include an outer surface 356 that provides the tissue/occluder interface, as discussed herein. The outer surface 356 can include a variety of shapes, including a planar shape or curved shaped. For example, in one embodiment, the cross-sectional shape of the circumferential ring member 354 can include a semi-circular shape having an outer surface 356 that is planar, i.e., flat.

Various components of the collapsible frame 342, e.g., the struts 352, and the circumferential ring member 354, may be formed from a variety of metals and/or metal alloys. As discussed herein, the collapsible frame 342 can be self-expanding. Examples of suitable materials for the collapsible frame 342 include, but are not limited to, medical grade stainless steel (e.g., 316L), Nitinol, titanium, tantalum, platinum alloys, niobium alloys, cobalt alloys, alginate, or combinations thereof. In an additional embodiment, the struts 352 and the circumferential ring member 354 of the collapsible frame 342 may be formed from a shape-memory material, such as shape memory plastics, and other polymers. In one embodiment, the struts and the circumferential ring member can be formed from Nitinol. Other materials are also possible.

In various embodiments, the center shaft 346 can be formed of the same materials as the struts 352 and the circumferential ring member 354. In some embodiments, the center shaft 346 can be formed of a rigid material so as not to flex under compression. Examples of rigid materials that can be used to form the center shaft can include polymers such as plastics, thermosetting plastics, thermoplastics, or a metal or metal alloy. In one embodiment, the struts 352, the center shaft 346, and the circumferential ring member 354 can be manufactured in a molding process to form a unitary collapsible frame 342 without the need to couple the struts 350 to the center shaft 346 and the circumferential ring member 354. Alternatively, the struts 350, the center shaft 346, and the circumferential ring member 354 can be derived (e.g., laser cut, water cut) from a single tubular segment.

In various embodiments, the collapsible frame 342 can include a support band 358. The support band 358 can have a unitary ring configuration that is generally smaller in diameter than the circumferential ring member 354 of the occluder pads 338 and 340. In various embodiments, the support band 358 can be radially positioned along the struts 352 and between the apex 348 of the center shaft 346 and the circumferential ring member 354. In some embodiments, the support band 358 can be radially positioned along the struts 352 an equal distance between the apex 348 of the center shaft 346 and the circumferential ring member 354. In other embodiments, the support band 358 can be radially positioned along the struts 352 closer to the circumferential ring member 354 relative to the apex 348 of the center shaft 346.

In various embodiments, the support band 358 can be coupled to the struts 352 in a variety of ways. In one embodiment, the support band 358 is coupled to the struts 352 by extending the support band 358 through openings 360 in the struts 352. For example, FIG. 3C illustrates two struts 352 of the present invention. As shown in FIG. 3C, the struts 352 include surfaces that define opening 360 through the struts 352 so as to allow the support band 358 to extend through the opening 360 of each strut 352 as it extends around the collapsible frame 342. In such embodiments, the struts can include reinforcement material proximal and adjacent to the openings 360 in the struts so as to provide additional structural support to the collapsible frame 342 in the area proximal and adjacent to the opening 360. In other embodiments, the support band 358 can be heat or chemically welded to each strut 352. In another embodiment, the struts 352 can include notches into which the support band 358 is positioned as it extends around the collapsible frame 342. In various embodiments, the support band 358 can be wrapped around each strut 350 so as to form a loop around each strut 350 as it extends around the collapsible frame 342.

The support band 358 can be formed of a number of materials. Examples can include elastic materials such as natural and/or synthetic rubbers, and natural and/or synthetic elastomers, and the like. Other materials can include flexible polymeric materials, metals, and metal alloys.

In one embodiment, the support band 358 can impart a resistive force to the collapsible frame as it is compressed against tissues surrounding a defective occlusion. This resistive force aids the struts in maintaining their substantially convex curves when the occluder pads are compressed against tissue surrounding a defective occlusion, as well as after the first and second occluder pads have been adjusted to a desired distance and secured at that distance. The support band 358 also helps to prevent the collapsible frame 342 and the cover 344 from being inverted from their radial position around the center shaft 346 when the distance between the first and second occluder pads is being adjusted. In other words, the support band 358 helps to prevent the occluder pads 338, 340 from being inverted like an umbrella in a strong wind.

In various embodiments, the cover 344 can extend across an area between the apex 348 of the center shaft 346 and the circumferential ring member 354 so as to cover an outer surface 362 of the collapsible frame 342. In one embodiment, the cover 344 extends from the apex 348 toward the circumferential ring member 354 where it bends around the circumferential ring member 354 back toward the apex 348 of the center shaft 346 so as to cover the outer surface 362 and an inner surface 364 of the collapsible frame 342. In an alternative embodiment, the cover 344 can be attached to the collapsible frame 342 in a weave configuration such that cover 344 alternates between the outer surface 362 of one strut 352 and the inner surface 364 of an adjacent strut 352 and so on until all the struts 352 have been covered. In such an embodiment, the weaving of the cover 344 can preclude the need to fasten the cover 344 to the struts 352 using chemical or mechanical fasteners, as will be discussed herein.

The cover 344 can be coupled to the collapsible frame 342 by any suitable method. For example, the cover 344 can be coupled to the collapsible frame 342 using a chemical adhesive and/or heat. In some embodiments, the cover 344 can be mechanically coupled to the collapsible frame 342 using fasteners such as sutures, clips, and the like.

In one embodiment, cover 344 can be constructed of a material sufficiently thin and pliable so as to permit radially-collapsing of the cover for delivery by catheter to a desired location. The cover 344 can be constructed of a material that can be either synthetic and/or biologic. In various embodiments, the material used to form the cover, whether synthetic or biologic, or a combination of synthetic or biologic can be substantially impermeable to fluids and solids. Possible synthetic materials include, but are not limited to, expanded polytetrafluoroethylene (ePTFE), polytetrafluoroethylene (PTFE), polystyrene-polyisobutylene-polystyrene (SIBS), polyurethane, segmented poly(carbonate-urethane), Dacron, polyethlylene (PE), polyethylene terephthalate (PET), silk, urethane, Rayon, Silicone, or the like. In an additional embodiment, the material can also include metals, such as stainless steel (e.g., 316L) and Nitinol. These materials can be in a woven, a knit, a cast or other known physical solid and fluid-impermeable configurations.

Possible biologic materials include, but are not limited to, autologous, allogeneic or xenograft material. These include explanted veins, pericardium, facia lata, harvested cardiac valves, bladder, vein wall, various collagen types, elastin, intestinal submucosa, and decellularized basement membrane materials, such as small intestine submucosa (SIS) or umbilical vein.

Figure 4A:
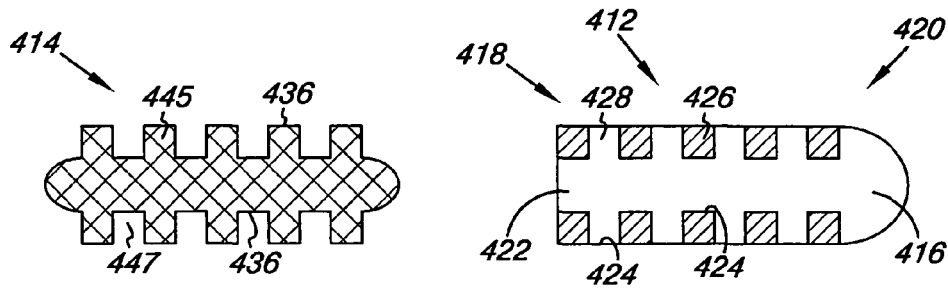
FIGS. 4A-4D illustrate an embodiment of the first and second elongate bodies of an occlusion device according to the present invention.
Figure 4B:
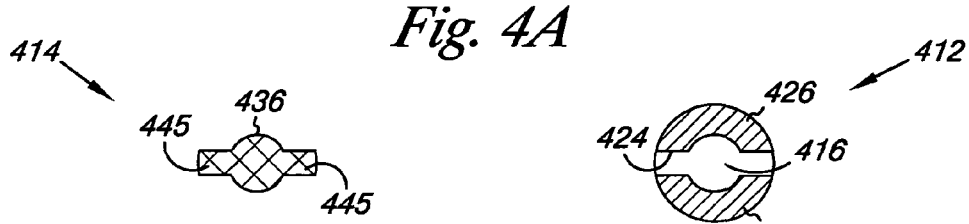
Figure 4C:
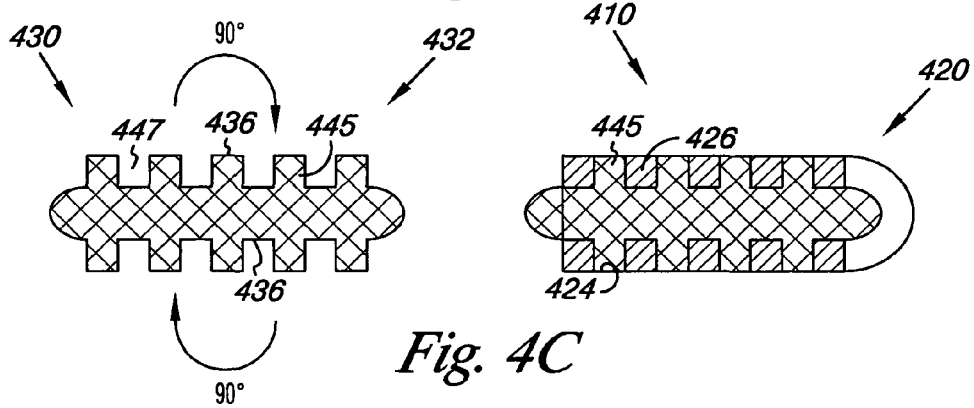
Figure 4D:
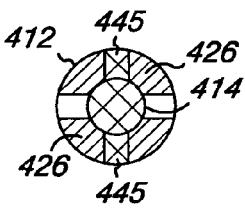

As discussed herein, first and second elongate bodies of the occlusion device can include a variety of configurations. Another such configuration is illustrated in FIGS. 4A-4D. FIG. 4A illustrates a side-view of the first and second elongate bodies. FIG. 4B illustrates a front-on view of the first and second elongate bodies. FIGS. 4C and 4D illustrate the second elongate body being rotated 90 degrees so as to lock the second elongate body within the first elongate body. As shown in FIG. 4A, occlusion device 410 includes the first and second elongate bodies 412 and 414. The first elongate body 412 includes lumen 416 extending between the proximal end 418 and the distal end 420 of the first elongate body 412. As shown in FIG. 4A, lumen 416 is in communication with opening 422.

In the embodiment illustrated in FIG. 4A, lumen 416 defines the first engaging element 424, which forms the projections 426 and indentations 428 arranged along the longitudinal axis of the first elongate body 412. As shown in FIG. 4A, the projections 426 and indentations 428 are arranged in an opposing and alternating configuration along a longitudinal axis of the first elongate body 412, such that each indentation 428 and each projection 426 oppose each other along the longitudinal axis, as discussed herein. As shown in FIG. 4B, the projections 426 help to define an opening in the lumen 416 that is a mirror image of the second engaging elements 436 of the second elongate body 414. As will be discussed herein, the mirror image opening in the lumen 416 allows the second elongate body 414 to travel within the lumen 416 from the proximal end 418 toward the distal end 420 of the first elongate body 412.

The second engaging elements 436 of the second elongate body 414 extend from the proximal end 430 toward the distal end 432 of the second elongate body 414. As shown in FIG. 4C, as the second engaging elements 436 extend toward the distal end 432, a portion of the second engaging elements 436 form a number of projections 445 and indentations 447. The projections 445 are designed so as to include a shape and size that are slightly smaller than the shape and size of the indentations 428 of the first engaging elements 424. In various embodiments, the indentations 428 of the first engaging elements 424 provide a space in which projections 445 on the second engaging elements 436 can engage so as to lock the second elongate body 414 within the first elongate body 412, as will be discussed herein.

In various embodiments, the first and second elongate bodies 412 and 414 of the occluder device 410 illustrated in FIGS. 4A-4D can include occluder pads coupled thereto, as discussed herein. In one embodiment, the first and second engaging elements 424 and 436 of the first and second elongate bodies 412 and 414 respectively can interact to adjust a distance between the first and the second occluder pads and to secure the adjusted distance. In some embodiments, adjusting the distance between the first and second occluder pads includes moving the first and second occluder pads in a first direction (a first direction—e.g., first and second occluder pads move towards each other). In other embodiments, adjusting the distance between the first and second occluder pads include moving in either the first direction or a second direction opposite the first direction (e.g. first and second occluder pads can be moved toward each other or away from each other). For example, in one embodiment, the second elongate body 414 can be positioned such that the second engaging elements 436 of the second elongate body 414 are in line with the mirror image opening defined by lumen 416 of the first engaging elements 428.

Once positioned, the deployment shaft, as discussed herein, can be coupled to the second elongate body 414. A pushing force can be exerted on the deployment shaft to move the second elongate body 414 within the lumen 416 of the first elongate body 412 toward the distal end 420 so as to decrease the distance between the first and second occluder pads, as discussed herein. When a desired distance between the first and second occluder pads has been reached, the second elongate body can be rotated so as to lock the occluder pads at the adjusted distance. If the distance between the occluder pads is further adjusted, the second elongate body can be further rotated to re-align the engaging elements 436 of the second elongate body 414 with the mirror image opening defined by lumen 416 of the first engaging elements 428 so as to allow a further adjustment in the first and/or second direction, as discussed herein.

FIG. 4D provides an illustration in which the second elongate body 414 has been turned within the lumen 416 of the first elongate body 412 substantially 90 degrees to lock the relative position of the first and second occluder pads. Once locked, the occluder pads maintain the adjusted distance between them.

As shown in FIGS. 4C and 4D, the rotating the second elongate body relative the first elongate body allows the projections 445 of the second engaging elements 436 to occupy the space defined by the indentations 428 of the first engaging elements 424. The surfaces of the projections 426 of the first engaging elements 424 preclude a linear movement of the second elongate body 414 because the surfaces of the projections 426 preclude the second elongate body from moving toward the distal end 420 of the first elongate body 412 and from backing out of the first elongate body 412, to effectively, lock in the adjusted distance, as discussed herein. The locked first and second elongate bodies maintains the compression upon surfaces surrounding both sides of a defective occlusion even while the occlusion device is subjected to the mechanical motion of the beating heart.

In some embodiments, the distance between the first and second occluder pads can be increased and/or decreased simply by unlocking the occlusion device by a further rotation of the second elongate body clockwise or counterclockwise so that the second engaging elements 436 of the second elongate body 414 is again in line with the mirror image opening defined by lumen 416 of the first engaging elements 428.

In another embodiment, the first and second elongate bodies of the occlusion device can include elongate bodies having surfaces that define threads that can engage to allow for changes to the distance between the occluder pads. For example, in the embodiment illustrated in FIG. 5, the first elongate body 512 includes the lumen 516 having the first engaging elements 524 that defines threads 570. The second engaging elements 536 of the second elongate body 514 includes a surface that defines threads 572.

Figure 5:
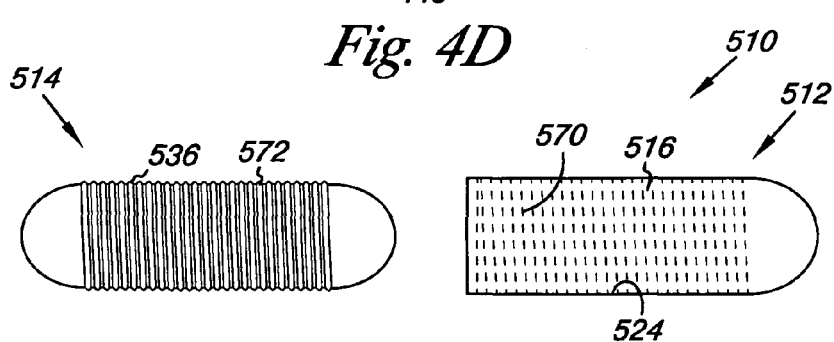
FIG. 5 illustrates another embodiment of the first and second elongate bodies of an occlusion device according to the present invention.

In the embodiment illustrated in FIG. 5, the first and second engaging elements 524 and 536 of the first and second elongate bodies 512 and 514 respectively can interact to adjust the distance between the first and second occluder pads, which are coupled thereto, as discussed herein. For example, the deployment shaft, as discussed herein, can be used to thread the second elongate body 514 into the first elongate body 512 a desired distance so as to adjust the distance between the first and the second occluder pads.

In one embodiment, the threads on the center shaft of the second occluder pad can be designed to accommodate a clockwise and a counterclockwise motion of the deployment shaft, as discussed herein. In addition, the threads on the center shaft can terminate at a predetermined point along the inner surface of center shaft. The predetermined point can be designed to prevent rotational torque exerted on the deployment shaft from screwing further into the center shaft such that any rotational torque by the deployment shaft at the predetermined point is transferred to the second elongate body 514. That is, if the deployment shaft continues to rotate once it reaches the predetermined point within the center shaft, the rotational torque is imparted to the second elongate body 514. This rotational torque causes the second elongate body 514 to rotate such that the threads 572 on the second elongate body 514 begin to engage with the threads 570 on the first elongate body 512. As the second elongate body 514 is threaded into the first elongate body 512, the distance between the occluder pads begins to decrease.

In one embodiment, the threads 572 on the second elongate body 514 and the threads 570 on the first elongate body 512 are designed to preclude an unthreading of the first and second elongate bodies 512 and 514. Such a design can include, but is not limited to, threads that deform as they engage with each other. In such an embodiment, the distance between the first and second occluder pads can be adjusted to a desired distance and locked at that distance. The self locking nature of the elongate bodies maintains the compression upon surfaces surrounding both sides of a defective occlusion even while the occlusion device is subjected to the mechanical motion of the beating heart, as will be discussed herein.

Figure 6:
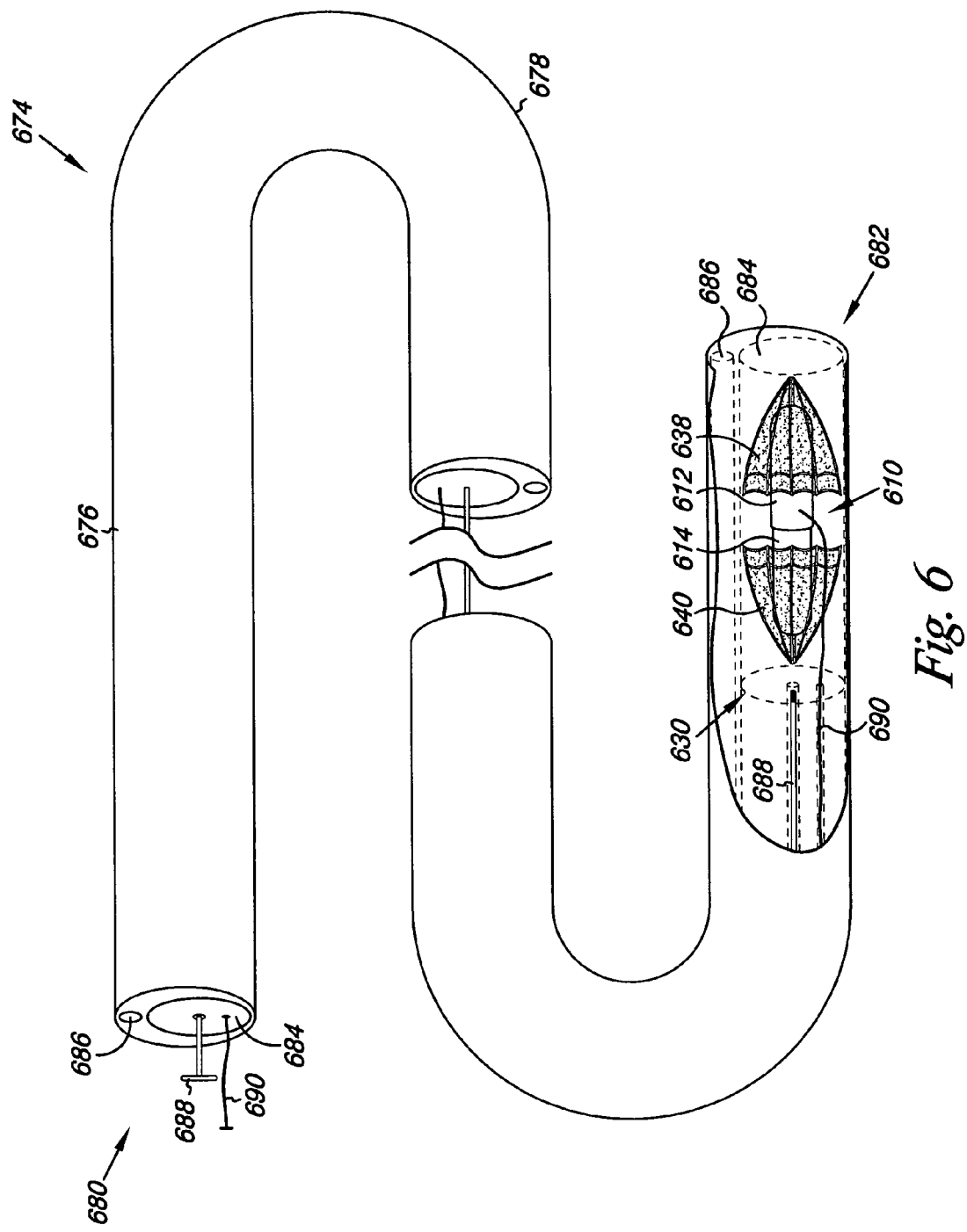
FIG. 6 illustrates an embodiment of a system of the present invention.

FIG. 6 illustrates an embodiment of a system 674 that includes the occlusion device 610 of the present invention. System 674 also includes a catheter 676. The catheter 676 includes an elongate body 678 having a proximal end 680 and a distal end 682. In various embodiments, the occlusion device 610 can be located between the proximal end 680 and the distal end 682 of the catheter 676. The catheter 676 includes lumen 684. In various embodiments, the lumen 684 can extend longitudinally toward the distal end 682 of the catheter 676. In one embodiment, lumen 684 extends from the proximal end 680 to the distal end 682 of the catheter 676.

The catheter 676 can further include a guidewire lumen 686. The guidewire lumen 686 can extend within the elongate body 678 of the catheter 676 from the proximal end 680 to the distal end 682 of the catheter 676. In various embodiments, the guidewire lumen 686 can receive a guidewire for positioning the catheter 676 and the occlusion device 610 within a heart chamber (e.g., a right atrium of a patient). In various embodiments, the guide wire lumen 686 and the lumen 684 can include various configurations. For example, in some embodiments, the guidewire lumen and the lumen can include a dual lumen configuration within the catheter. In other embodiments, the guidewire lumen and the lumen can include a coaxial configuration within the catheter.

In various embodiments, the first and second occluder pads 638 and 640 can be collapsed into a collapsed configuration and inserted into the lumen 684 of the catheter 676, as shown in FIG. 6. The collapsed configuration of the first and second occluder pads 638 and 640 may be of any shape suitable for easy passage through the lumen 684 of the catheter 676 and proper deployment out the distal end 682 of the catheter. For example, the first and second occluder pads 638 and 640 may have a relatively elongated collapsed configuration wherein the first and second occluder pads 638 and 640 are collapsed along their longitudinal axis. This collapsed configuration can be achieved simply by applying pressure around the circumference of the first and second occluder pads 638 and 640 and toward the elongate bodies 612 and 614 of the first and second elongate bodies 612 and 614. Loading such a device into the catheter 676 may be done at the time of manufacture or at the time of implantation.

In various embodiments, the system 674 can include the deployment shaft 688 positioned within lumen 684, as discussed herein. The deployment shaft 688 can be used to deploy the occlusion device 610 from the catheter 676. In one embodiment, the deployment shaft 688 can be positioned adjacent the proximal end 630 of the second elongate body 614. As discussed herein, the deployment shaft 688 can include threads for engaging the threads of the center shaft of the second occluder pad 644. In such embodiments, the deployment shaft 688 can be threaded to the center shaft of the second occluder pad, as discussed herein. The deployment shaft 688 can move within the lumen 684 of the catheter 676 to deploy the occlusion device 610 from the lumen 684 of the catheter 676. In some embodiments, a pushing force and/or a rotational torque can be applied to the deployment shaft 688 to move the second elongate body 614 within the lumen of the first elongate body 612 so as to adjust a distance between the first and second occluder pads and to lock the adjusted distance, as discussed herein. In other embodiments, a pulling force can be exerted on the deployment shaft 688 to pull the occlusion device 610 back into the catheter 676 in the event the occlusion device 610 is to be retrieved from the human body, as will be discussed herein.

In various embodiments, system 674 can include one or more pulling members 690. The pulling member 690 can be positioned longitudinally within the lumen 684 of the catheter 676 between the proximal and distal ends 680 and 682 of the catheter 676. In various embodiments, the pulling member 690 can be used to pull the first occluder pad 638 toward the second occluder pad 640 to help with adjusting the distance between the first and second occluder pads 638 and 640, as will be discussed herein.

The embodiments of the present invention further include methods for occluding a defective occlusion using the various embodiments of the occlusion device of the present invention, as discussed herein. FIGS. 7A-7D illustrate various method embodiments that can be implemented to occlude a PFO. However, the methods illustrated in FIGS. 7A-7D can be implemented to occlude other defective occlusions in the human body.

One method for occluding the PFO includes introducing the catheter, as discussed herein, into the venous system of the patient using a minimally invasive percutaneous, transluminal catheter based delivery system. A PFO is an opening in the atrial septum at the location of the fossa ovalis. A unique aspect of the fossa ovalis is its location relative to the orifice of the inferior vena cava. Since the fossa ovalis is located above and to the left of the orifice of the inferior vena cava, the occlusion device can be deployed upon entering the right atrium from the orifice of the inferior vena cava. For example, a guidewire can be positioned within the venous system and advanced to the right atrium of a patient. In one embodiment, the right atrium can be entered via the orifice of the inferior vena cava. The catheter, including the occlusion device, as described herein, can be positioned over the guidewire and the catheter advanced so as to position the distal end of the catheter proximal to or adjacent the septal wall at the location of the PFO.

In one embodiment, radiopaque markers on the catheter and/or the occlusion device can be used to help position the occlusion device within the right atrium and/or to traverse the PFO with the occlusion device, as will be discussed herein. In addition, orientation and visualization of the occlusion device and the various components of the occlusion device (e.g., first and second elongate bodies and first and second occluder pads) may be accomplished through the use of any combination of echogenic, angioscopic, ultrasound and fluoroscopic visualization techniques.

Figure 7A:
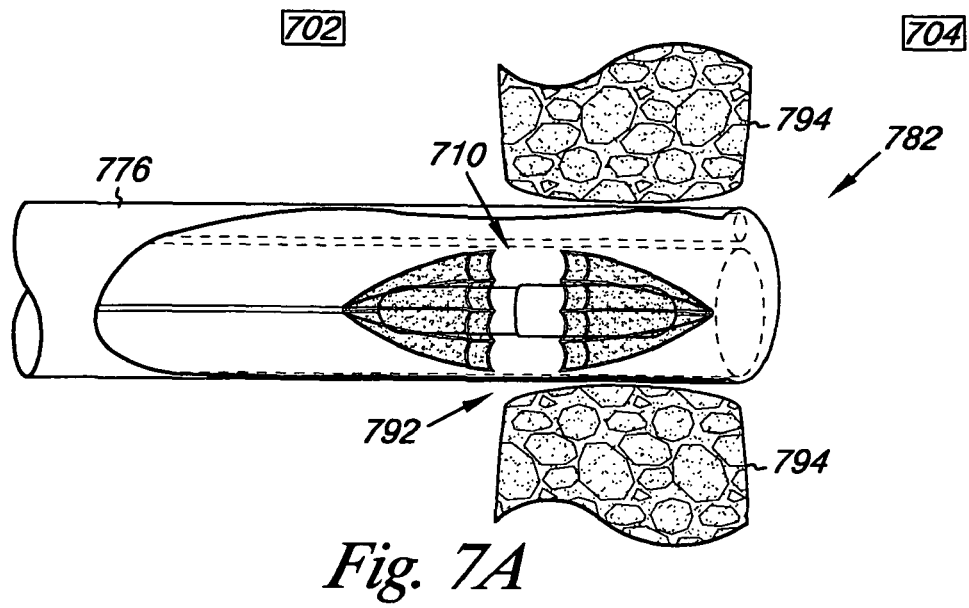
FIGS. 7A-7D illustrate an embodiment of the system in relation to a septum of the heart.

As shown in FIG. 7A, the method can include traversing the PFO 792 with a portion of the occlusion device 710. In the embodiments illustrated in FIGS. 7A-7D, the portion of the occlusion device can include all or a portion of the first elongate body 712 of the occlusion device 710.

Figure 7B:
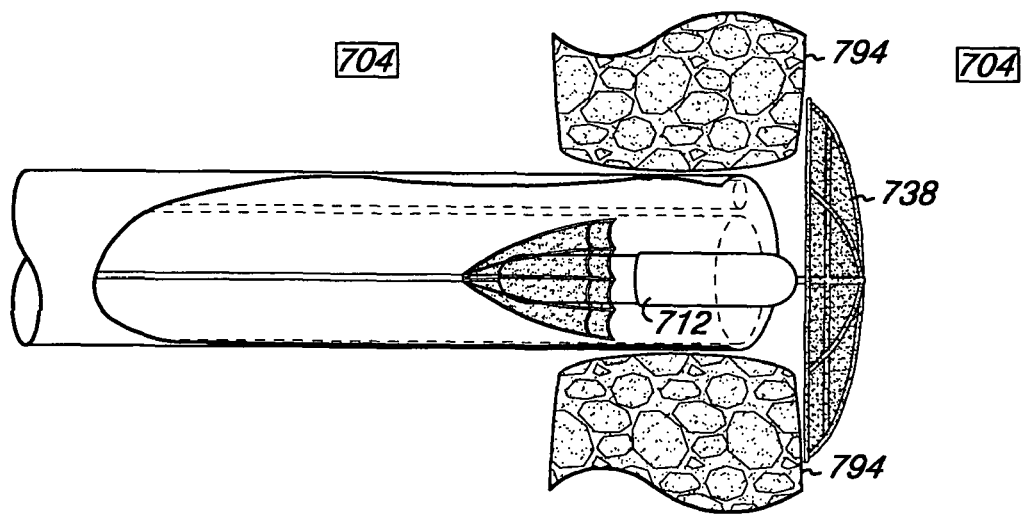

In various embodiments, traversing the PFO 792 can include the catheter 776 having the occlusion device 710 therein. The catheter 776 enters the PFO 792 from the right atrium 702 and traverses the PFO 792 such that the distal end 782 of the catheter 776 projects into the left atrium 704. Once the distal end 782 of the catheter 776 is present in the left atrium 704, a pushing force can be exerted on the occlusion device 710 by the deployment shaft 788 to push a portion of the first elongate body 712 of the occlusion device 710 from the distal end 782 of the catheter 776 to deploy the first occluder pad 738 on a first side 794 of the PFO 792, as shown in FIGS. 7A and 7B.

In an alternative embodiment, the method for traversing the PFO can include the catheter having the occlusion device therein and positioning the catheter proximal the second side of the defective occlusion. Once positioned, a pushing force can be exerted upon the occlusion device to push a portion of the first elongate body of the occlusion device through the PFO to deploy the first occluder pad on the first side of the defective occlusion.

In another embodiment, the method for traversing the PFO can include the catheter having the occlusion device therein, and retracting the catheter to allow the first elongate body of the occlusion device to self-deploy from the catheter on the first side of the defective occlusion. Once the first occluder pad has been deployed on the first side of the PFO, the first occluder pad expands to its predefined shape since it is no longer constrained by the lumen of the catheter.

Figure 7C:
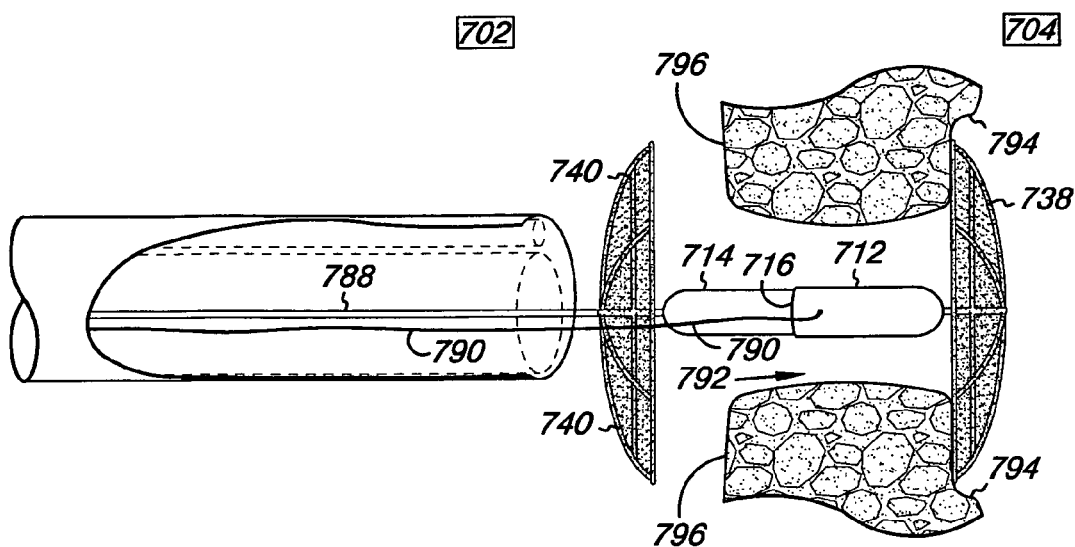

In various embodiments, the method for occluding the PFO 792 can further include deploying the second occluder pad 740 on a second side 796 of the PFO 792. To do this, the distal end 782 of the catheter 776 can be positioned proximal to or adjacent the second side 796 of the PFO 792 (e.g., within the right atrium) and a pushing force can be exerted on the occlusion device 710 by the deployment shaft 788 to push the second elongate body 714 of the occlusion device 710 from the distal end 782 of the catheter 776 to deploy the second occluder pad 740 on the second side 796 of the PFO 792, as shown in FIG. 7C.

In an alternative embodiment, deploying the second occluder pad can include a catheter having the occlusion device therein and retracting the catheter to self-deploy the second occluder pad from the occlusion device on the second side of the defective occlusion. Once the second occluder pad has been deployed on the second side of the defective occlusion, the second occluder pad also expands to its predefined shape since it is no longer constrained by the lumen of the catheter.

In various embodiments, the method can further include adjusting the distance between the first and second occluder pads 712 and 714 to occlude the PFO 792. In one embodiment, the distance between the first and second occluder pads can be adjusted by imparting a pulling force on the first occluder pad 738 so as to compress tissue surrounding the first side 794 of the PFO 792 with the first occluder pad 712 while moving the second occluder pad 740 toward the first occluder pad 738. To do this, the pulling member 790 can be reversibly attached to first elongate body 712 of the occlusion device 710 and a pulling force can be exerted on the pulling member 790 so as to pull the first elongate body 712 toward the second occluder pad 740, as shown in FIG. 7C.

Figure 7D:
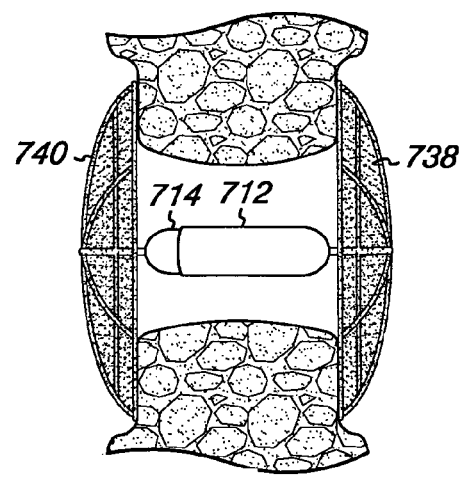

In various embodiments, moving the second occluder pad 740 toward the first occluder pad 738 can include imparting a pushing force on the second occluder pad 740 so as to compress tissue surrounding the second side 796 of the PFO 792 with the second occluder pad 740 while maintaining the pulling force on the first occluder pad 738. To do this, the pushing force can be exerted on the second occluder pad 738 by the deployment shaft 788 to move the second elongate body 714, onto which the second occluder pad 740 is coupled, into the lumen 716 of the first elongate body 712, as described herein. As the second elongate body 714 moves into the first elongate body 712, the distance between the first and second occluder pads 738 and 740 decreases. As the distance decreases, the second occluder pad begins to compress the tissue surrounding the PFO 792 on the second side 796 of the PFO 792, as shown in FIGS. 7C and 7D. This compression of the tissues serves to anchor the occlusion device 710 to the first and second sides 794 and 796 of the PFO 792 and to occlude the PFO 792 by blocking the PFO 792 with the first and second occluder pads 738 and 740.

In various embodiments, the reversible attachment of the pulling member 790 can include a variety of configurations and designs. For example, in one embodiment, the pulling member 790 can be coupled to the first elongate body 712 with a fastener that is designed to release the pulling member 790 when a pulling force exceeds a preset threshold. In such an embodiment, the operator can pull the pulling member to impart the compression of the first occluder pad 712 upon tissue surrounding the PFO 792. When the operator is ready to release the pulling member 790 from the first elongate body 712, the operator can increase the pulling force until it exceeds the preset threshold and the pulling member 712 breaks away from the fastener. In such embodiments, the preset threshold of the fastener can be set so as to not exceed a pulling force that could cause the first occluder pad to invert, as discussed herein.

In another embodiment, the pulling member 790 can coupled to the first elongate body 712 with a fastener that is designed to release the pulling member 790 when the pulling member 790 is rotated. In such an embodiment, an operator can pull on the pulling member 790 so as to impart compression by the first occluder pad 738 upon tissue surrounding the PFO 792. When the operator is ready to release the pulling member 790 from the first elongate body 712, the operator can rotate the pulling member clockwise or counterclockwise to release the pulling member 790 from the fastener.

After the distance between the first and second occluder pads has been adjusted, the operator can secure the adjusted distance. In some embodiments, the operator need not take any additional actions to secure the adjusted distance. For example, referring back to the embodiments illustrated in FIGS. 2A-2D, the elongate members 234 expand when they engage with indentation 228 of the first elongate body 212. If the operator does not desire to adjust the distance between the first and second occluder pads further, nothing more need be performed by the operator because the locking surface 239 of the second engaging element 236 can engage the surface defining the projections 226 to lock the second elongate body 214 within the lumen 216 of the first elongate body 212.

In another example, in the embodiment illustrated in FIGS. 4A-4D, the rotation of the second elongate body to engage the first engaging member with the second engaging member effectively locks the first and second occluder pads at the adjusted distance.

Once the operator has adjusted the distance between the first and second occluder pads and locked the adjusted distance, the operator can pull the catheter including the components of the catheter (e.g., deployment shaft, pulling member, and guidewire) from the patient leaving the occlusion device behind.

As the reader will appreciate, the occlusion device includes a number of designs and configurations, and thus, the occlusion device illustrated in the various Figures are not intended to limit the present disclosure to the embodiment illustrated.

While the present invention has been shown and described in detail above, it will be clear to the person skilled in the art that changes and modifications may be made without departing from the scope of the invention. As such, that which is set forth in the foregoing description and accompanying drawings is offered by way of illustration only and not as a limitation. The actual scope of the invention is intended to be defined by the following claims, along with the full range of equivalents to which such claims are entitled.

In addition, one of ordinary skill in the art will appreciate upon reading and understanding this disclosure that other variations for the invention described herein can be included within the scope of the present invention. For example, the catheter can be coated with a non-thrombogenic biocompatible material, as are known or will be known.

In the foregoing Detailed Description, various features are grouped together in several embodiments for the purpose of streamlining the disclosure. This method of disclosure is not to be interpreted as reflecting an intention that the embodiments of the invention require more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separate embodiment.

What is claimed is:

1. An occluder device for occluding an opening in tissue, comprising:
   a first elongate body having an opening defined by a proximal end and a closed end defined by a distal end, and having an inner surface having first engaging elements defined by an alternating series of projections and indentations arranged to directly oppose each other and extend longitudinally along a lumen of the first elongate body, where a perpendicular cross-section of the alternating series of projections of the first elongate body includes a surface of each projection that is parallel to a longitudinal axis and defines a space between the projections;
a first occluder pad coupled to the distal end of the first elongate body;
a second elongate body having a proximal end and a distal end, and having a surface defining two elongate members that diverge away from each other as they extend from the proximal end toward the distal end of the second elongate body; each elongate member including a flange with a locking surface facing the proximal end of the second elongate body and configured to contact an opposing surface of the engaging element projections facing the distal end of the first elongate body thereby precluding the second elongate body from moving away from the distal end toward the proximal end of the first elongate body, the flange further including a compression surface having an oblique angle providing contact with the engaging element that forces the two elongate members towards each other allowing the flange to slide past engaging element projections as the second elongate body moves toward the distal end of the first elongate body responsive to a pushing force to the second elongate body; and
a second occluder pad coupled to the proximal end of the second elongate body;
where the device is deliverable from a single side of an opening in tissue by a single delivery catheter.

2. The device of claim 1, where the alternating series of projections include an opposing surface that is oriented substantially perpendicular to the longitudinal axis of the first elongate body.

3. The device of claim 1, where the first and second occluder pad interact to decrease the distance between the first and second occluder pad.

4. The device of claim 1, where the first and second occluder pads each include a collapsible frame and a cover over the collapsible frame.

5. The device of claim 4, where the collapsible frame includes a number of struts extending radially from a center shaft to a circumferential ring member of the collapsible frame.

6. The device of claim 5, including a support band axially coupled to the struts between the center shaft and the circumferential ring.

7. The device of claim 5, where the struts define a convex curve configuration.

8. A method, comprising:
traversing a defective occlusion with a body portion of an occlusion device;
deploying a first occluder pad coupled on a first side of the body portion from a delivery catheter to a first side of the defective occlusion, where the first side of the body portion includes a first elongate body having first engaging elements defined by an alternating series of projections and indentations along a longitudinal axis within a lumen of the first elongate body;
deploying a second occluder pad coupled on a second side of the body portion from the delivery catheter to a second side of the defective occlusion, where the second side of the body portion includes a second elongate body including a second engaging element where the first and second occluder pads are deployed from the delivery catheter;
moving the second engaging element to a locked position with the first engaging elements at one of a plurality of discrete distances between the first and second occluder pads to prevent the second elongate body from travelling within the lumen along the longitudinal axis of the first elongate body;
moving the second engaging element to a unlocked position to adjust a length of the body portion by disengaging the second engaging element from the first engaging elements to allow the second engaging element to move along the longitudinal axis within the lumen of the first elongate body to another one of the plurality of discrete distances between the first and second occluder pads;
applying a pushing force to the second elongate body to move the second elongate body; and
locking the body portion at the other one of the plurality of discrete distances between the first and second occluder pads by moving the second engagement to the locked position with the first engaging elements, to anchor the occlusion device to tissues surrounding the defective occlusion, and occlude the defective occlusion.

9. The method of claim 8, where adjusting includes pulling the first occluder pad against the first side of the defective occlusion.

10. The method of claim 8, where adjusting includes pushing the second occluder pad against the second side of the defective occlusion.

11. The method of claim 8, where adjusting includes imparting a pulling force on the first occluder pad so as to compress tissue surrounding the first side of the defective occlusion with the first occluder pad while moving the second occluder pad toward the first occluder pad.

12. The method of claim 11, where adjusting includes imparting a pushing force on the second occluder pad so as to compress tissue surrounding the second side of the defective occlusion with the second occluder pad while maintaining the pulling force on the first occluder pad.

13. The method of claim 8, where adjusting includes applying a compression force upon tissues surrounding the first side and the second side of the defective occlusion by surfaces of the first and second occluder pads so as to anchor the first and second occluder pads to tissues surrounding the defective occlusion and to occlude the defective occlusion by blocking the opening with the first and second occluder pads.

14. The method of claim 8, where re-adjusting the length includes rotating a first telescoping member of the body portion 90 degrees with respect to a second telescoping member and moving the first and second occluder pads toward each other.

15. The method of claim 8, where adjusting the distance between the first and second occluder pads includes moving the first and second occluder pads away from each other.

16. An occluder device, comprising:
a first elongate body having an opening defined by a proximal end and a closed end defined by a distal end, and having an inner surface having first engaging elements defined by an alternating series of projections and indentations arranged to directly oppose each other and extend longitudinally along a lumen of the first elongate body, where a perpendicular cross-section of the alternating series of projections of the first elongate body includes a surface of each projection that is parallel to a longitudinal axis and defines a space between the projections;
a second elongate body having an outer surface having a corresponding series of interlocking projections and indentations that extend longitudinally along the second elongate body to define second engaging elements, where, in a first radial position of the second elongate body with respect to the first elongate body, the first and second engaging elements are disengaged;

a first occluder pad coupled to the first elongate body; and a second occluder pad coupled to the second elongate body; and means for reversibly locking the first and second occluder pads at a distance relative to each other to occlude a defective occlusion, where in a second radial position of the second elongate body with respect to the first elongate body, the first and second engaging elements are engaged by a pushing force applied to the second elongate body;

where the device is deliverable from a single side of an opening in tissue by a single delivery catheter.

17. The system of claim 16, including means for adjusting the distance of the first and second occluder pads relative to each other.

18. The system of claim 17, where means for adjusting the distance of the first and second occluder pads includes compressing tissue surrounding at least two sides of the defective occlusion.

19. The system of claim 16, where the first and the second occluder pads include a collapsible frame having a support band axially coupled to the collapsible frame.

20. The device of claim 16, where the lumen of the first elongate body includes channels extending from a distal end to a proximal end of the first elongate body that are partially defined by the surface of each projection that is parallel to the longitudinal axis, where the second engagement elements travel within the channels in either direction along the longitudinal axis to adjust the length of the first and second occluder pads relative to each other.

21. The device of claim 16, where the lumen of the first elongate body includes a plurality of slots defined by an opposing surface of the alternating series of projections that is oriented substantially perpendicular to the longitudinal axis of the first elongate body, where the second engagement elements travel into the slots engaging the first engaging elements and the second engaging elements to prevent the second elongate body from travelling within the lumen along the longitudinal axis.

* * * * *